US012629502B1

(12) United States Patent
Lim

(10) Patent No.: US 12,629,502 B1
(45) Date of Patent: May 19, 2026

(54) VENOUS DRAINAGE CATHETER FOR NORMOTHERMIC REGIONAL PERFUSION

(71) Applicant: Kok Hoo Lim, Beavercreek, OH (US)

(72) Inventor: Kok Hoo Lim, Beavercreek, OH (US)

( * ) Notice: Subject to any disclaimer, the term of this patent is extended or adjusted under 35 U.S.C. 154(b) by 0 days.

(21) Appl. No.: 19/208,385

(22) Filed: May 14, 2025

(51) Int. Cl.
| | |
|---|---|
| *A61B 17/12* | (2006.01) |
| *A61B 90/00* | (2016.01) |
| *A61M 1/36* | (2006.01) |
| *A61M 25/00* | (2006.01) |
| *A61M 25/10* | (2013.01) |
| *A61B 17/00* | (2006.01) |

(52) U.S. Cl.
CPC ....... *A61M 25/10* (2013.01); *A61B 17/12031* (2013.01); *A61B 17/12109* (2013.01); *A61B 17/12136* (2013.01); *A61B 90/39* (2016.02); *A61M 1/3603* (2014.02); *A61M 25/0043* (2013.01); *A61B 2017/00557* (2013.01); *A61B 2090/3937* (2016.02); *A61M 2025/0008* (2013.01); *A61M 2025/1052* (2013.01); *A61M 2205/583* (2013.01)

(58) Field of Classification Search
CPC .......... A61M 25/10; A61M 2025/0008; A61M 2025/1052; A61M 1/3603; A61M 60/36; A61B 17/12109; A61B 17/12
See application file for complete search history.

(56) References Cited

U.S. PATENT DOCUMENTS

| | | |
|---|---|---|
| 10,278,384 B2 | 5/2019 | Tillman et al. |
| 2015/0342177 A1 | 12/2015 | Hassanein et al. |
| 2021/0289771 A1 | 9/2021 | Gharb |
| 2023/0166099 A1* | 6/2023 | Harris ................. A61M 60/295 600/16 |

FOREIGN PATENT DOCUMENTS

| | | |
|---|---|---|
| EP | 4252536 A1 | 10/2023 |
| WO | 2000018226 A2 | 4/2000 |

* cited by examiner

*Primary Examiner* — Deanna K Hall

(57) ABSTRACT

A venous drainage catheter is an apparatus for normothermic regional perfusion (NRP) to prevent blood flow to the lower limbs when assessing organ function for patients. The apparatus includes a main cannula, an inflation cannula, and an occluding balloon. The main cannula draws blood from the inferior vena cava (IVC). The blood then flows into a reservoir of a cardiopulmonary bypass circuit (CPB) machine. Once inserted within the IVC and inflated, the occluding balloon prevents blood flow towards the lower limbs of the patient. The inflation cannula enables the occluding balloon to inflate and deflate while inserted within the IVC. A main cannula inlet receives blood flowing down within the IVC and the main cannula outlet disperses the blood towards the reservoir of the CPB machine. A plurality of holes positioned about the main cannula inlet drains the blood flow from the IVC to the reservoir.

18 Claims, 14 Drawing Sheets

13

13

VENOUS DRAINAGE CATHETER FOR NORMOTHERMIC REGIONAL PERFUSION

FIELD OF THE INVENTION

The present invention relates generally to medical equipment. More specifically, the present invention provides a femoral veinous catheter for normothermic regional perfusion in order to salvage organs for transplantation.

BACKGROUND OF THE INVENTION

When liver and kidneys are harvested after circulatory arrest, the conventional method places the harvested organs in a sterile bag within a basin of icy sterile saline to preserve the organs before transplantation. Also known as standard cold storage (SCS) these organs are then transported in the icy sterile saline to the facilities for transplantation. Currently, many of the organs are discarded due to doubt about the viability and quality of the organs to provide short- or long-term benefits due to the subjectivity in decision making. These organs would benefit from reliable pretransplant perfusion with oxygenated blood under physiological conditions.

Abdominal in situ normothermic regional perfusion (NRP) is a technique to restore circulation of the abdominal organs after circulatory death for the purpose of salvaging organs for transplantation. The technique uses cardiopulmonary bypass technology and extracorporeal membrane oxygenation to maintain near physiological state in the organs before transplantation. NRP allows for restoration of organ function in vivo, enables depleted ATP levels due to ischemia to be replenished, and allows for more accurate assessment of organ function. Furthermore, NRP reduces renal tubular injury and reduces incidence of delayed graft function.

NRP may be achieved through the following process:

Once circulatory death is pronounced and 5 minutes has passed, the abdomen is expeditiously prepped, draped, opened, and the upper abdominal aorta is cross clamped. This prevents oxygenated blood flow to perfuse the heart of the brain as the restoration of blood flow to the heat or brain may reanimate these organs. Abdominal aorta and inferior vena cava (IVC) are cannulated and connected to the cardiopulmonary bypass circuit (CPB) machine. Venous blood is drained from the IVC into a reservoir of the CPB machine, wherein the venous blood passes through a heat exchanger and membrane oxygenator. The oxygenated blood is then pumped back into the abdominal aorta to perfuse the organs being targeted.

SUMMARY OF THE INVENTION

Regular arterial and venous catheters are utilized for NRP resulting in the vessel cuadad to the cannulation may be receiving some blood flow. The resulting blood flow may be inadequate to meet the metabolic needs. The venous drainage from the IVC caudad to the cannulation site may be draining blood from lower limbs that are inadequately perfused. The current venous catheter may not provide adequate blood drainage in some cases. This may result in biomarkers released from ischemic tissues, interfering with blood tests to assess the viability of the organs during NRP, defeating part of the purpose of NRP.

The present invention is configured to overcome these issues wherein the abdominal aorta distal to the cannulation site on the abdominal aorta is clamped. This avoids perfusing the lower limbs and tissue caudad to the aortic clamp which is unnecessary for NRP. The present invention provides excellent venous drainage from the IVC. The present invention utilizes a occluding ballon that may be inflated near the site of insertion in the IVC, to occlude the IVC caudad to the cannulation site, ensuring that venous blood from the ischemic lower limbs will not drain into the reservoir of the connected CPB machine.

DETAILED DESCRIPTION OF THE INVENTION

Figure 1:
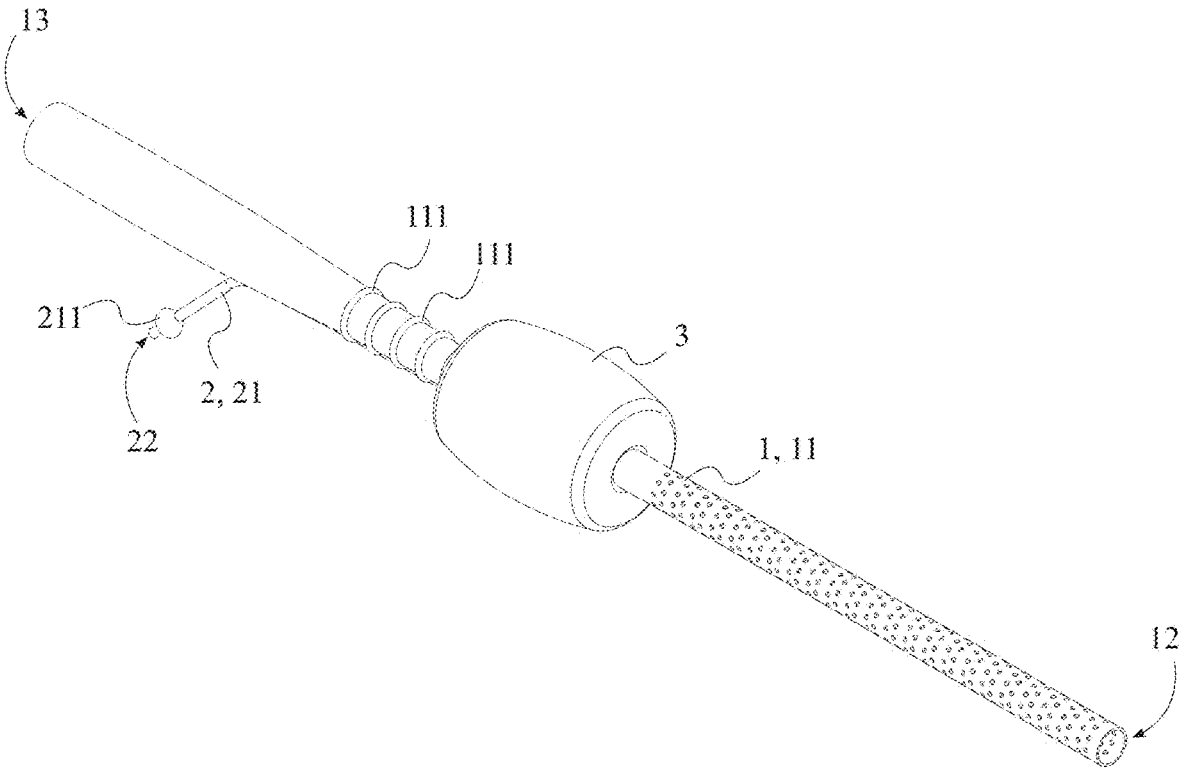
FIG. 1 is a top front right perspective view of the present invention.

All illustrations of the drawings are for the purpose of describing selected versions of the present invention and are not intended to limit the scope of the present invention.

The present invention is a venous drainage catheter that is used during normothermic regional perfusion (NRP) to prevent blood flow to the lower limbs when assessing organ function for an organ donor or patient. As can be seen in FIGS. 1-14, the present invention comprises at least one main cannula 1, an inflation cannula 2, and an occluding balloon 3. The at least one main cannula 1 is configured to draw blood from the inferior vena cava (IVC) wherein the blood flows into a reservoir 41 for a cardiopulmonary bypass circuit (CPB) machine 4. Once inserted within the IVC and inflated, the occluding balloon 3 prevents blood flow into the common iliac vein and external iliac vein, towards the lower limbs of the patient. The inflation cannula 2 enables the selective inflation and deflation of the occluding balloon 3 to facilitate the insertion and removal of the occluding balloon 3 along with the at least one main cannula 1 within the IVC. The at least one main cannula 1 comprises a main cannula body 11, a main cannula inlet 12, and a main cannula outlet 13. The main cannula inlet 12 and the main cannula outlet 13 correspond to the end openings of the main cannula body 11. The main cannula inlet 12 receives blood flowing down within the IVC and the main cannula outlet 13 disperses the blood towards the reservoir 41 of the CPB 4 machine. The main cannula outlet 13 may have a diameter of ⅜ of an inch or similar diameter to ensure proper blood flow from the at least one main cannula 1. The main cannula body 11 may be a length between 20-30 cm or any length wherein the main cannula body 11 may be properly inserted into the IVC The inflation cannula 2 comprises an inflation cannula body 21, an inflation cannula inlet 22, and an inflation cannula outlet 23. The inflation cannula inlet 22 and the inflation cannula outlet 23 correspond to the end openings of the inflation cannula body 21. The inflation cannula body 21 is laterally connected to the main cannula body 11. As a result, the inflation cannula body 21 and the main cannula body 11 form a single two-cannula structure that may be inserted within the IVC. The main cannula inlet 12 further comprises a plurality of holes 121. The plurality of holes 121 drains the blood flow from the IVC to the reservoir 41. In addition, the main cannula inlet 12 may be a tapered end to facilitate the insertion of the present invention into the IVC. The inflation cannula body 21 further comprises an inflation valve 211. The inflation valve 211 enables the user to selectively inflate or deflate the occluding balloon 3. The inflation cannula inlet 22 is positioned adjacent to the main cannula outlet 13. Consequently, this configuration maintains both cannula bodies are separate from each other, albeit next to one another. The occluding ballon is positioned about the center along the length of the main cannula body 11. Accordingly, this configuration ensures the occluding balloon 3 moves along with the main cannula body 11 as the main cannula inlet 12 is inserted into the IVC. Furthermore, this enables the occluding balloon 3 to be inserted within the IVC while the main cannula outlet 13 rests outside of the IVC, connected to the reservoir 41 of the CPB machine 4.

The general configuration of the present invention enables the at least one main cannula 1 and occluding balloon 3 to be inserted within the IVC preventing blood flow to the lower limbs of the patient. As can be seen in FIG. 1, the main cannula body 11 further comprises a plurality of markings 111. Thus, the plurality of markings 111 indicate to the user how deep the main cannula has been inserted into the IVC to ensure the occluding balloon 3 is properly positioned within the IVC to prevent blood flow. The plurality of markings 111 traverses radially about the main cannula body 11. So, the plurality of markings 111 may be visible to the user regardless of the rotational orientation of the main cannula 1 as the main cannula inlet 12 is inserted into the IVC. Each of the plurality of markings 111 being equally spaced from one another. Therefore, the plurality of markings 111 provides a precise measurement of how far the occluding balloon 3 is positioned within the IVC.

Figure 12:
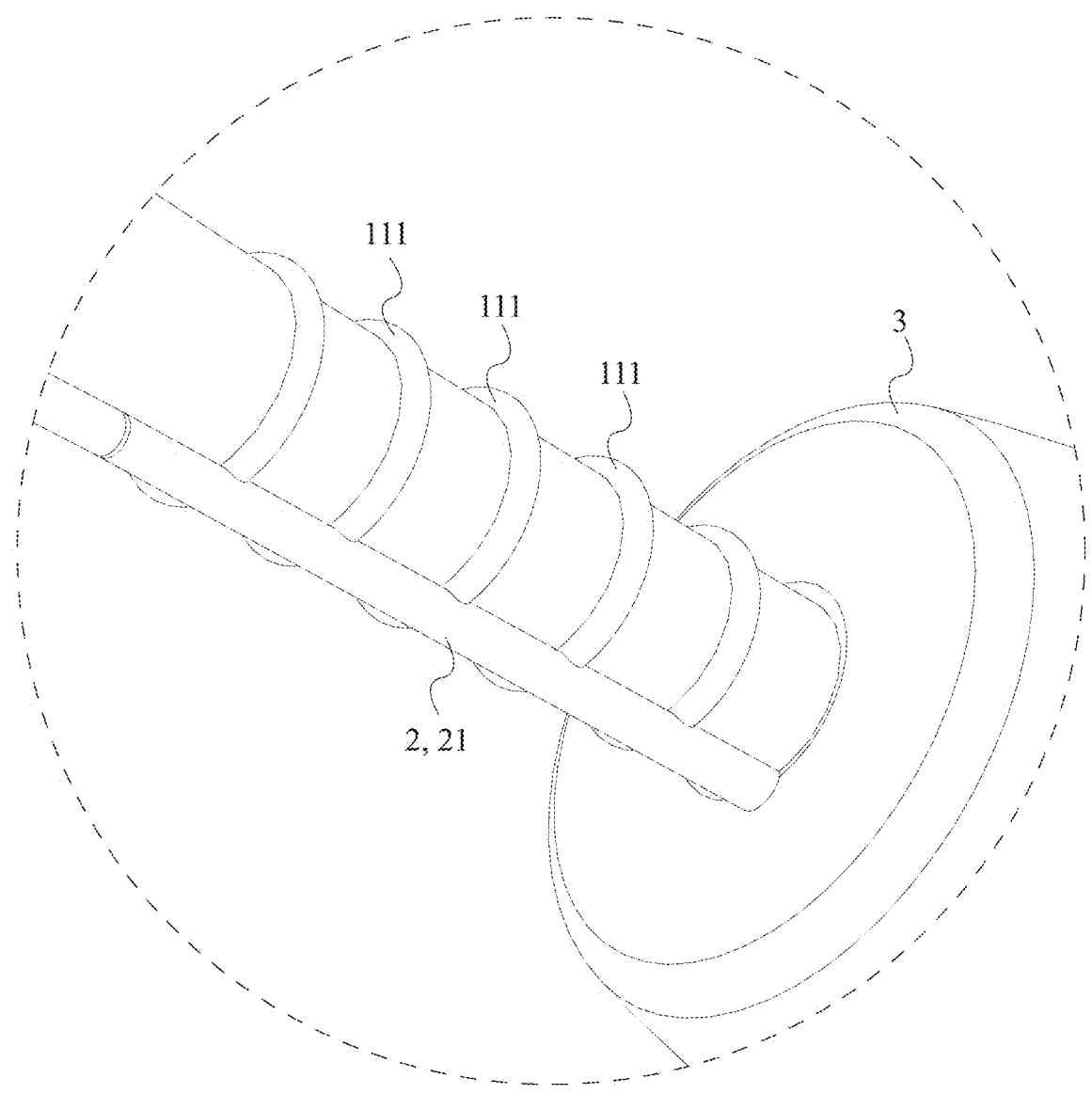
FIG. 12 is an enlarged detailed bottom rear right perspective view of the present invention.

Furthermore, the plurality of markings 111 is positioned adjacent to the occluding ballon as seen in FIG. 12. As a result, the user may count the number of markings 111 to identify how far the occluding balloon 3 is inserted into the IVC. The plurality of marking is positioned along the main cannula body 11 in between the main cannula outlet 13 and the occluding balloon 3. Consequently, this configuration ensures that the plurality of markings 111 is not obstructed by the inflation cannula inlet 22 or inflation valve 211.

Figure 11:
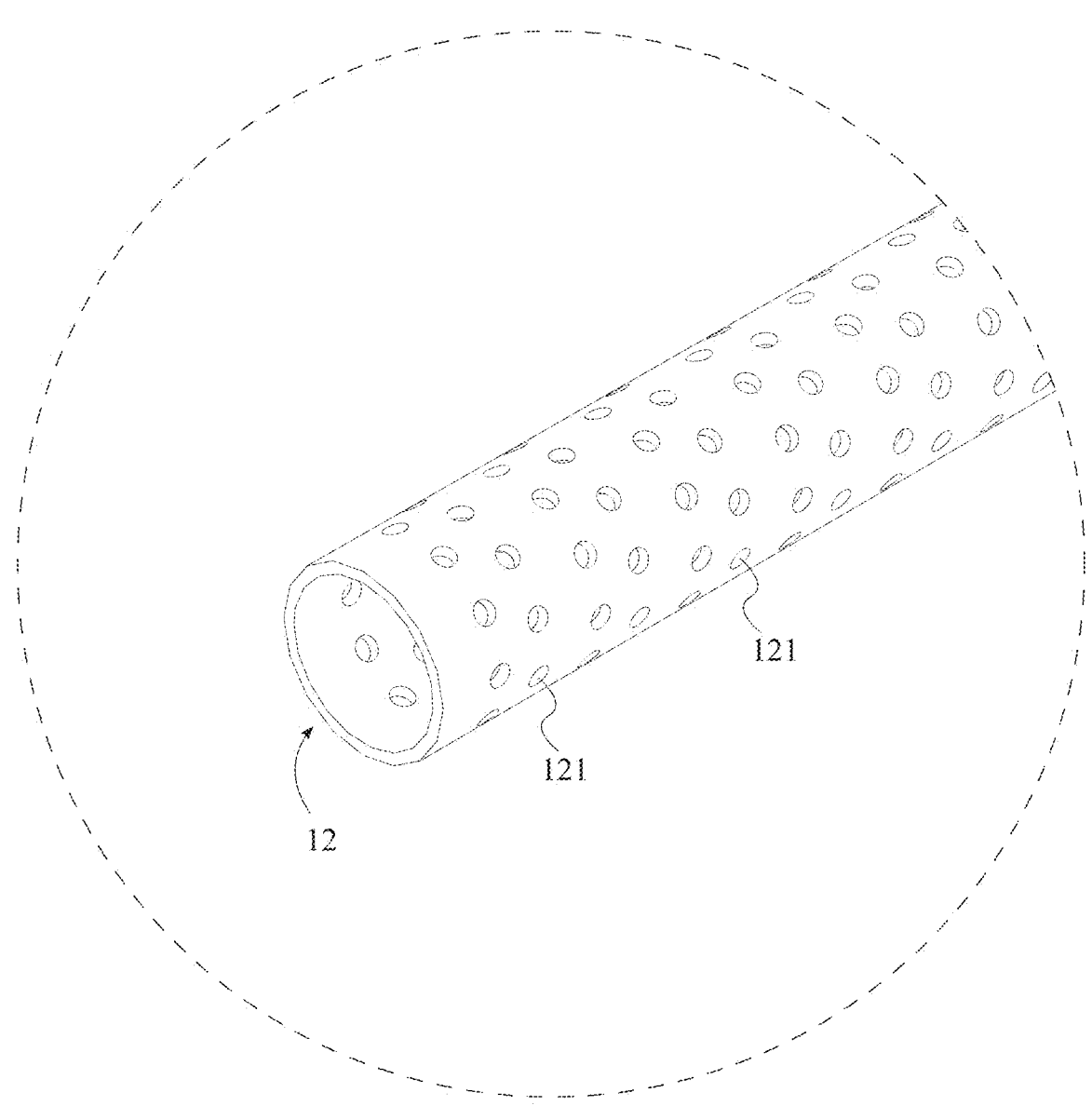
FIG. 11 is an enlarged detailed top front left perspective view of the present invention.

As can be seen in FIG. 11, the plurality of holes 121 is radially distributed about the main cannula inlet 12. Accordingly, this configuration ensures and even inflow of blood into the main cannula body 11. The plurality of holes 121 traverses through the main cannula inlet 12. Thus, there may be an unobstructed inflow of blood into the main cannula body 11. The plurality of holes 121 is distributed along the main cannula inlet 12 up until the occluding balloon 3. This provides an opening wherein blood may flow into the main cannula body 11 from the IVC and is not limited to a low flowrate due to the opening area. Further, the shape and size of the plurality of holes 121 may be modified according to the size of the main cannula inlet 12 to maintain efficient blood inflow from the IVC to the reservoir 41.

Figure 2:
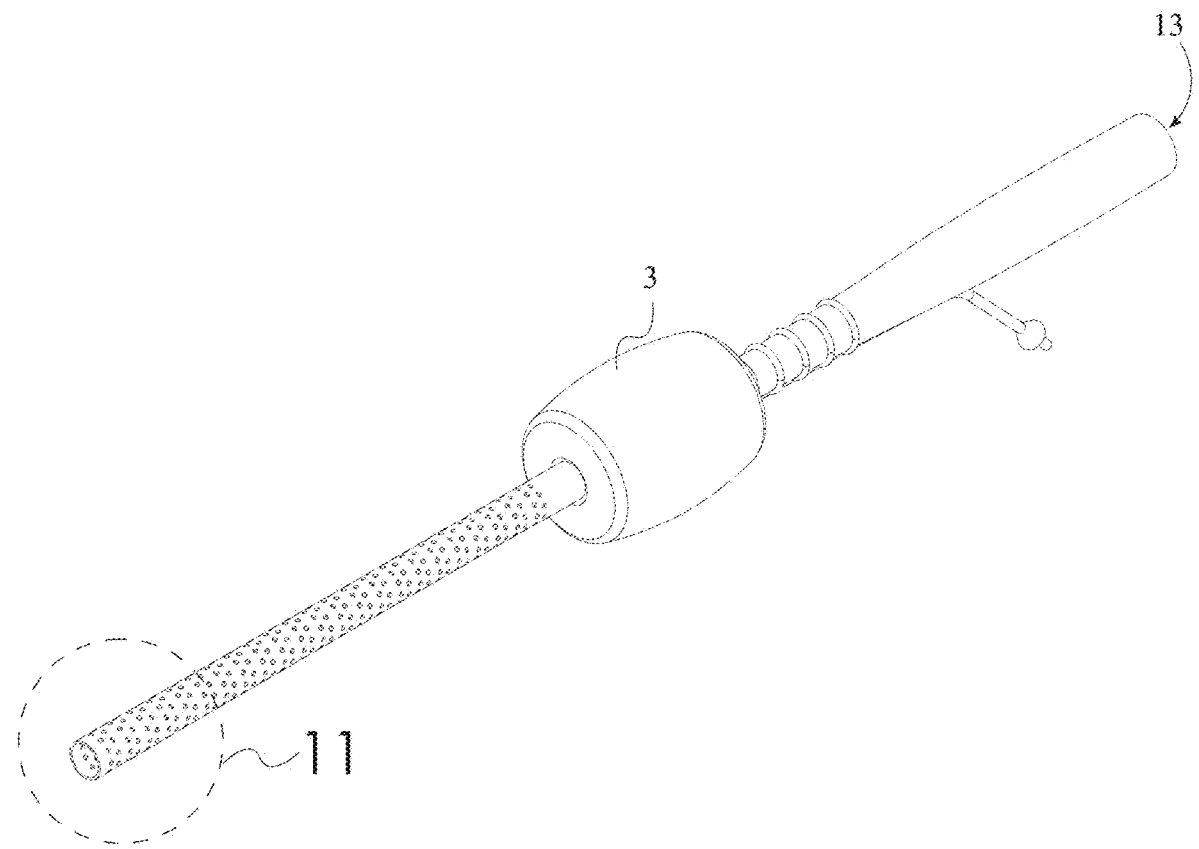
FIG. 2 is a top front left perspective view of the present invention.
Figure 3:
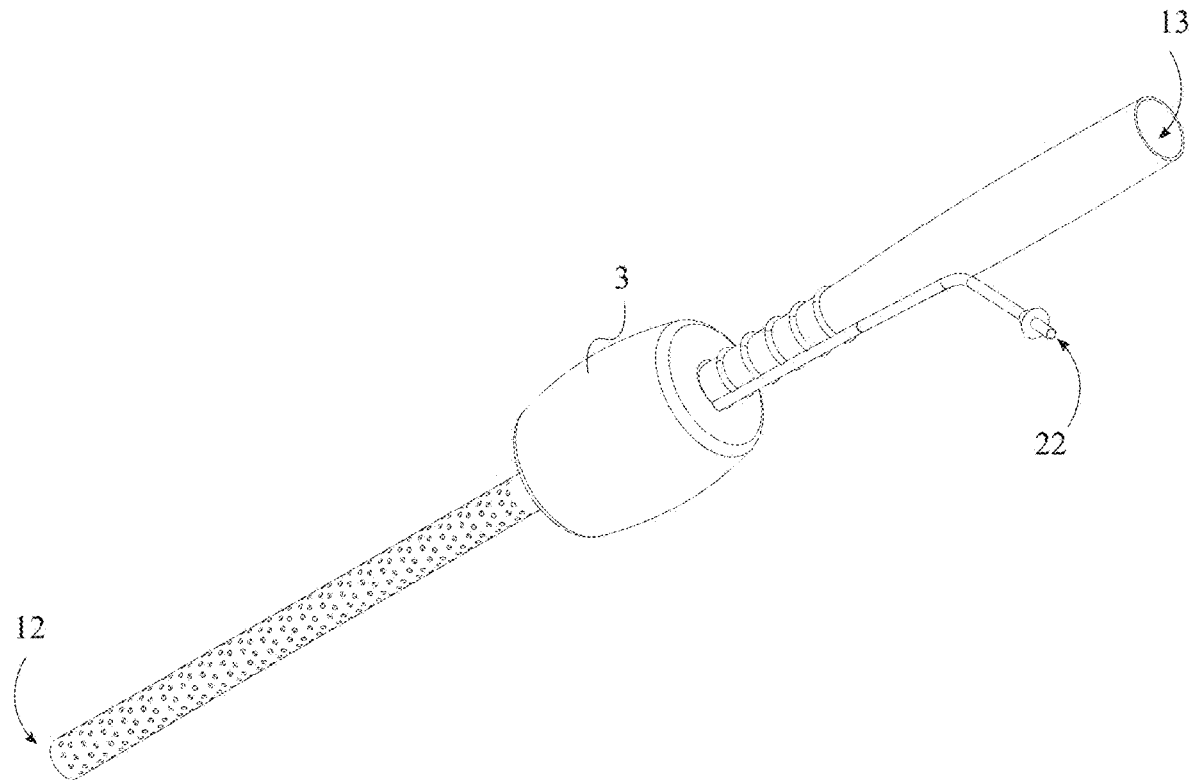
FIG. 3 is a bottom rear left perspective view of the present invention.
Figure 4:
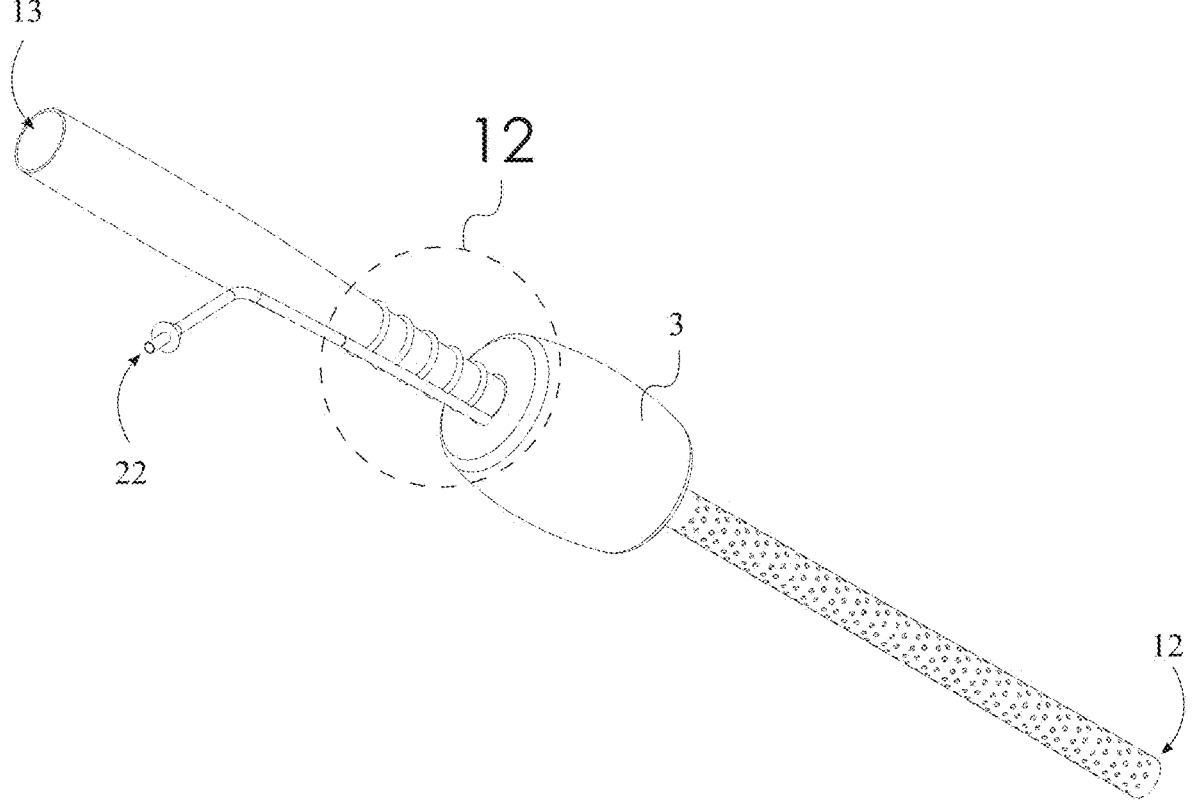
FIG. 4 is a bottom rear right perspective view of the present invention.
Figure 5:
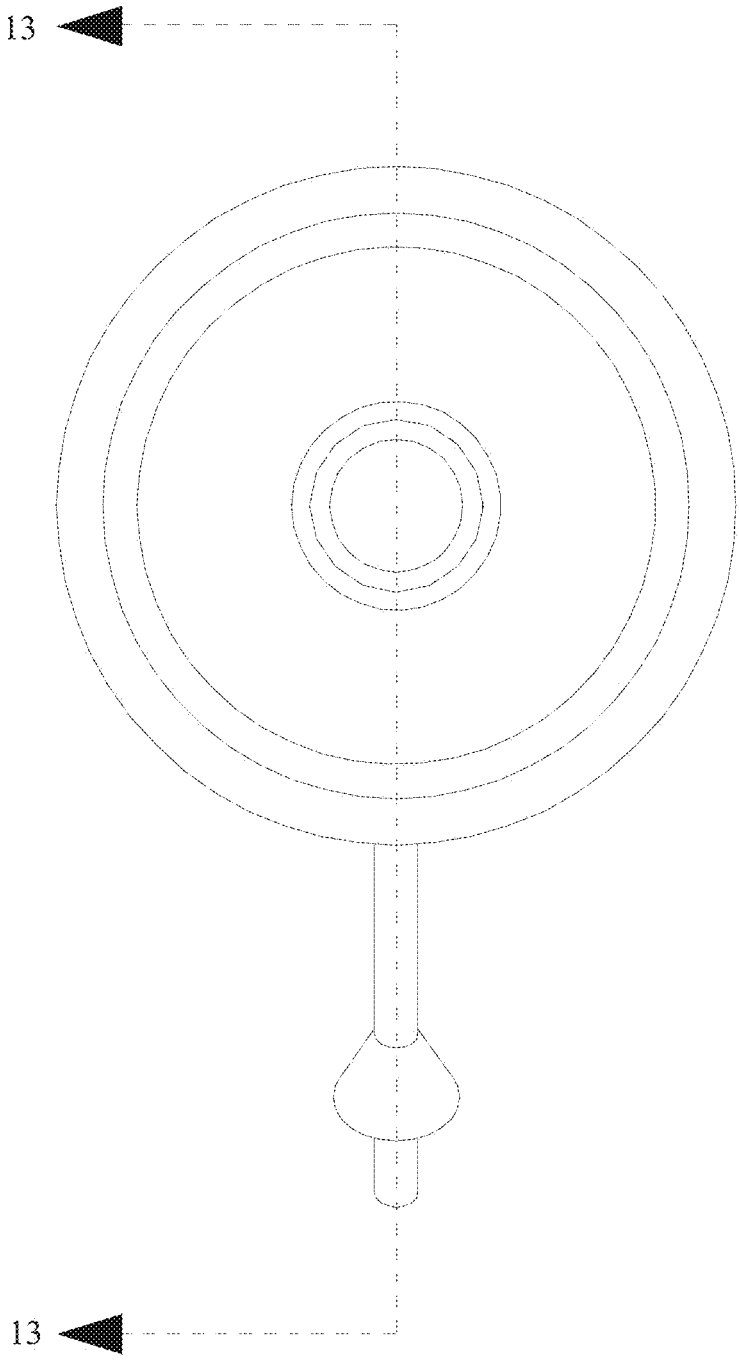
FIG. 5 is a front view of the present invention indicating the direction of section cut 13.
Figure 6:
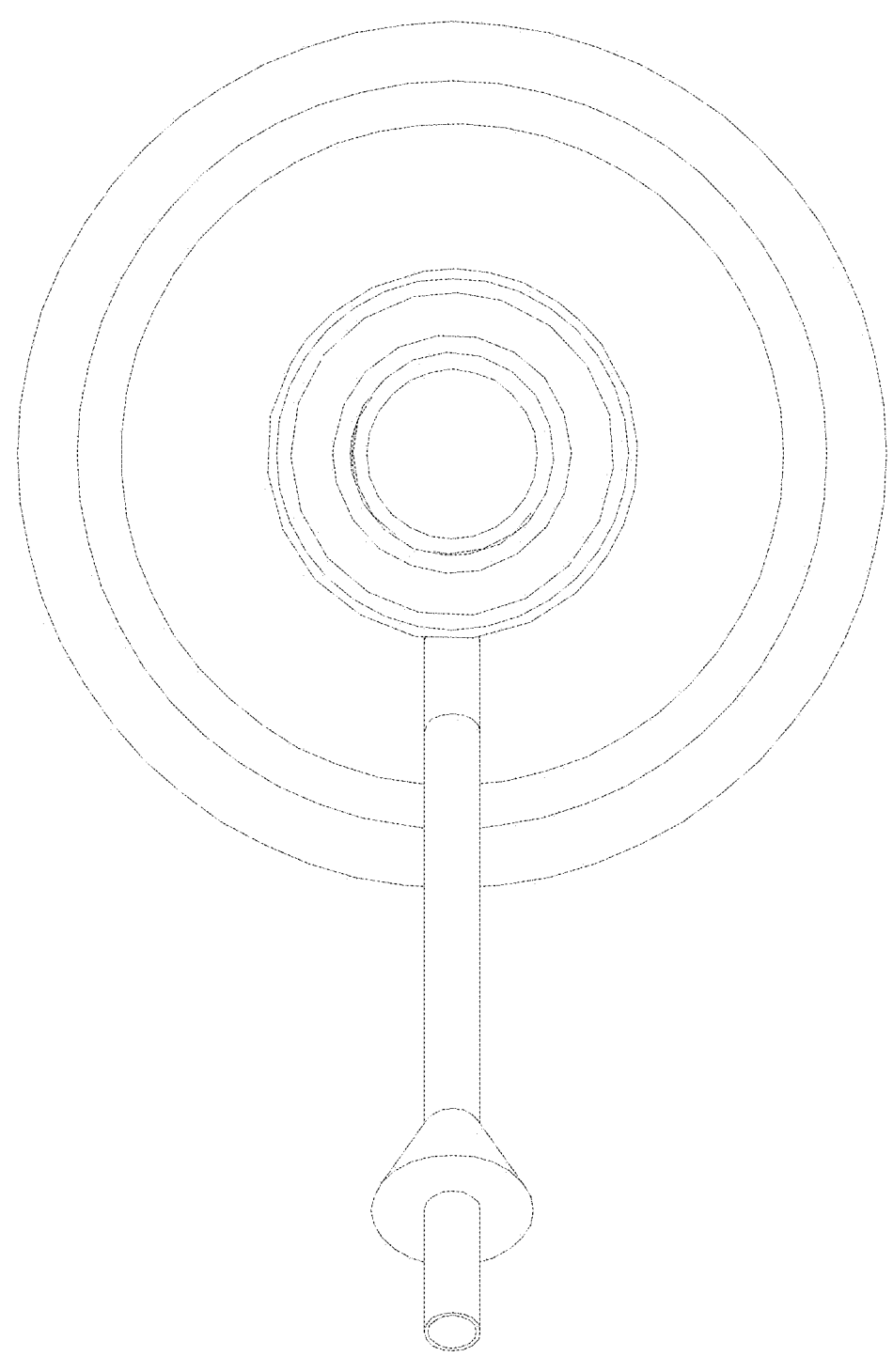
FIG. 6 is a rear view of the present invention.
Figure 7:
FIG. 7 is a top view of the present invention.
Figure 8:
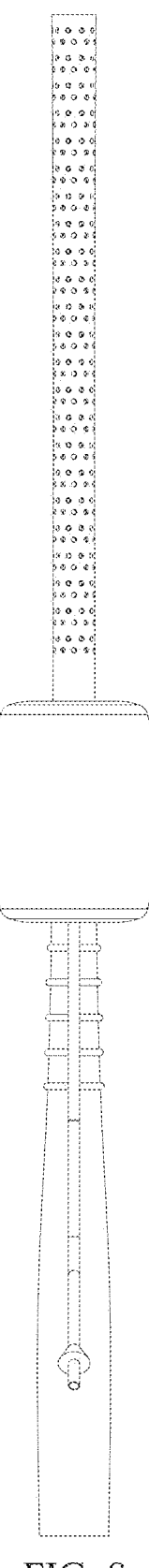
FIG. 8 is a bottom view of the present invention.
Figure 9:
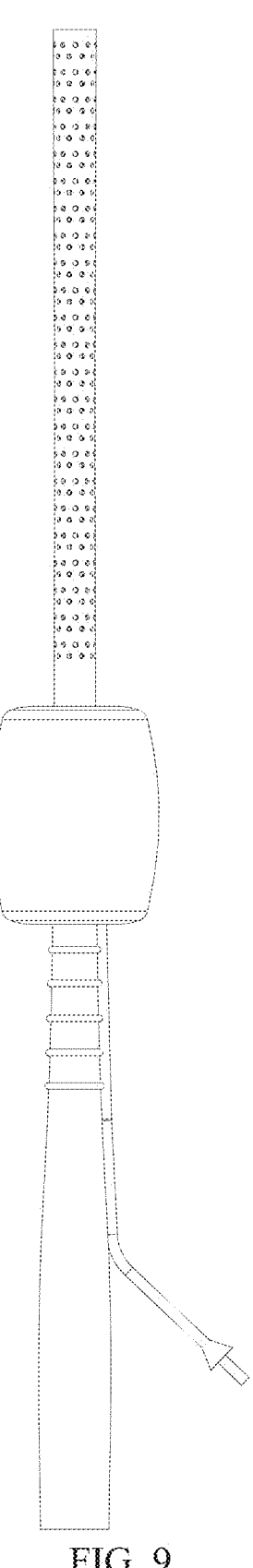
FIG. 9 is a right-side view of the present invention.
Figure 10:
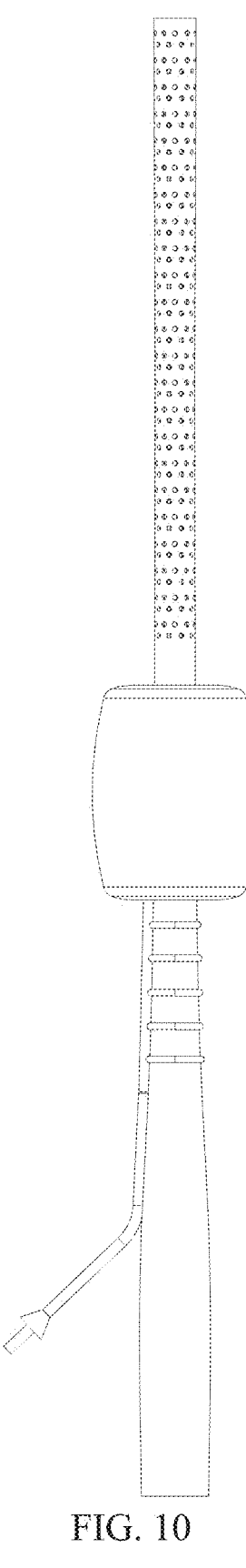
FIG. 10 is a left-side view of the present invention.

As can be seen in FIG. 2, the occluding balloon 3 is laterally connected around the main cannula body 11. So, the occluding balloon 3 moves in tandem with the main cannula body 11 as the main cannula inlet 12 is inserted into the IVC. The occluding balloon 3 may selectively inflate and deflate wherein as the occluding balloon 3 inflates, the outer surface of the occluding balloon 3 expands outwards away from the central axis of the main cannula body 11. The inflation cannula outlet 23 hermetically traverses into the occluding balloon 3. This configuration ensures that no fluid escapes the occluding ballon as the occluding ballon inflates. Furthermore, this ensures that the fluid does not escape the occluding ballon during a procedure. The inflation cannula inlet 22 is positioned offset from the main cannula outlet 13. As a result, the inflation cannula inlet 22 may be externally coupled to an air supply while the main cannula outlet 13 is coupled to the reservoir 41 of the CPB machine 4.

Figure 13:
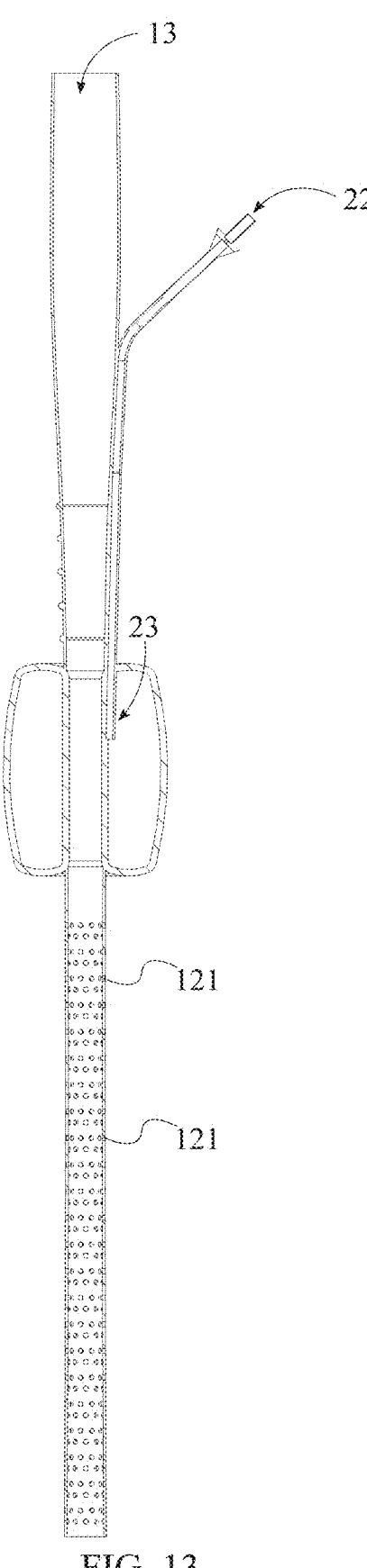
FIG. 13 is a left-side sectional view of the present invention taken along line 13-13 in FIG. 5.

In addition, the inflation valve 211 is in fluid communication with the inflation cannula 2, as shown in FIG. 13. Consequently, the inflation valve 211 enables the user to inflate or deflate the occluding ballon by sending air into the inflation cannula 2. The inflation valve 211 is positioned adjacent to the inflation cannula inlet 22. Furthermore, the inflation valve 211 prevents air from escaping backwards through the inflation cannula inlet 22 during a procedure.

Figure 14:
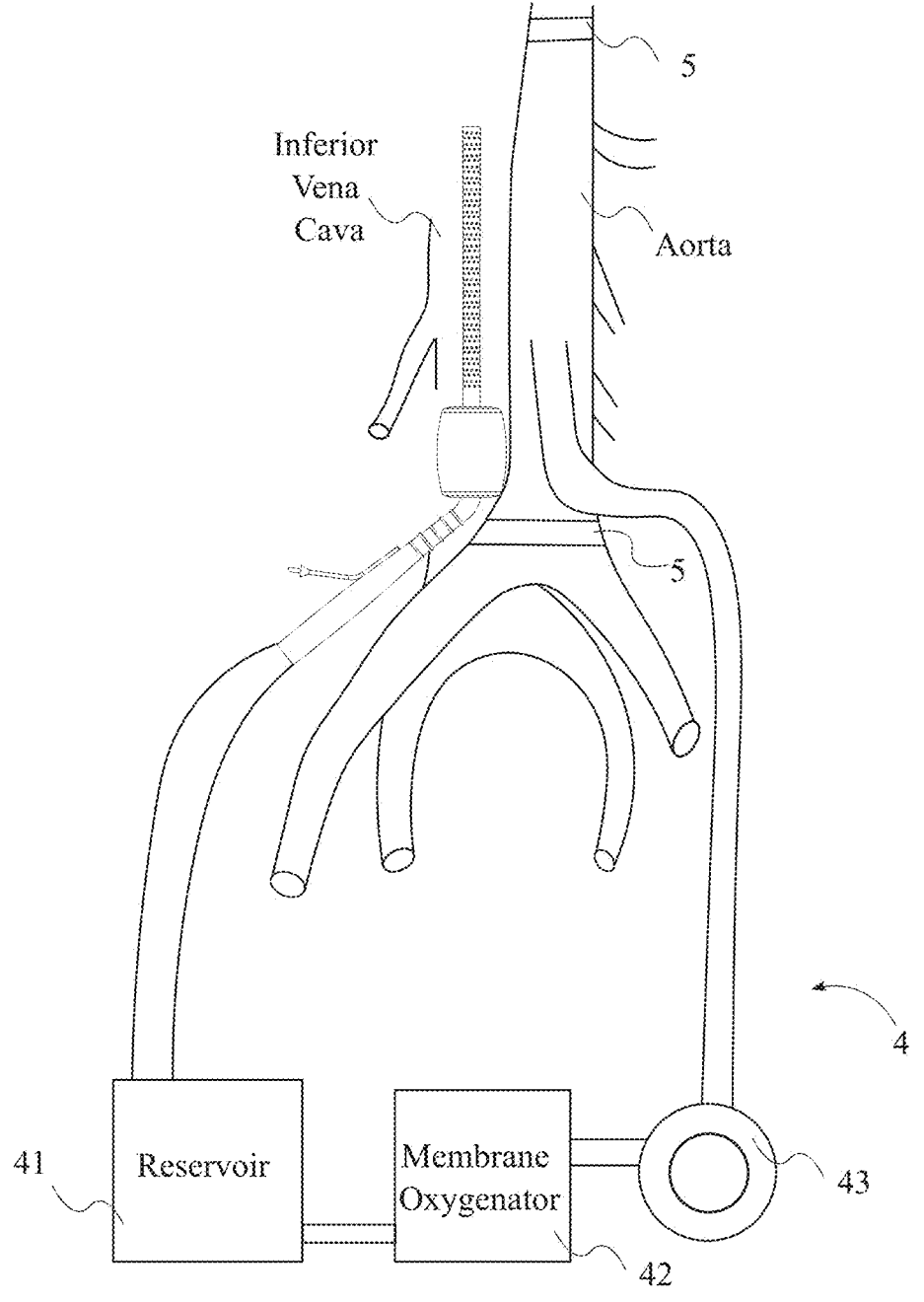
FIG. 14 is a schematic view showing the present invention, wherein the venous drainage catheter is shown inserted into the inferior vena cava.

As seen in FIG. 14, the present invention further comprises a cardiopulmonary bypass circuit (CPB) machine 4. The CPB machine 4 oxygenates and heats the blood drained from the IVC before being pumped back into the femoral artery of the patient. The cardiopulmonary bypass circuit machine 4 further comprises a reservoir 41, a membrane oxygenator 42, a pump 43, and at least one aortic cross clamp 5. The reservoir 41, membrane oxygenator 42, and pump 43 are in fluid communication in a series. Furthermore, the main cannula outlet 13 is in fluid communication with the reservoir 41. Consequently, blood may flow into the main cannula inlet 12 from the IVC, through the main cannula body 11, out of the main cannula outlet 13, and into the reservoir 41.

Exemplary Method of Use of the Present Invention

The present invention may be used for normothermic regional perfusion (NRP) to prevent blood flow to the lower limbs while assessing organ function for an organ donor or patient. Unlike the traditional procedure, the present invention enables the CPB machine 4 to perfuse abdominal organs and drain blood from these organs while avoiding the drainage of blood from tissues that are not adequately perfused. As can be seen in FIG. 14, the femoral artery and the femoral vein are cannulated, wherein the main cannula inlet 12 and occluding balloon 3 are inserted into the inferior vena cava (IVC). The occluding balloon 3 is inserted below the right gonadal vein and above the common iliac vein, external iliac vein and internal iliac vein. The occluding balloon 3 is inflated to direct blood flow into the main cannula inlet 12 and preventing blood flow down into the common iliac vein, external iliac vein or internal iliac vein. The femoral artery and femoral vein are connected to a CPB machine 4 wherein venous blood is drained from the IVC into the reservoir 41 of the CPB machine 4. The venous blood then passes through the membrane oxygenator 42 wherein the newly oxygenated blood is pumped back into the femoral artery of the patient. The descending thoracic aorta is cross clamped in two locations to prevent blood flow to the brain or heart. This configuration enables the liver, kidneys, and other abdominal organs to receive oxygenated blood while venous blood is drained into the reservoir 41 of a CPB machine 4 as needed. This enables the user to properly assess organ function without any interfering biomarkers.

Although the invention has been explained in relation to its preferred embodiment, it is to be understood that many other possible modifications and variations can be made without departing from the spirit and scope of the invention as hereinafter claimed.

What is claimed is:

1. A venous drainage catheter for normothermic regional perfusion comprising:
    at least one main cannula;
    an inflation cannula;
    an occluding balloon;
    the at least one main cannula comprising a main cannula body, a main cannula inlet, and a main cannula outlet;
    the inflation cannula comprising an inflation cannula body, an inflation cannula inlet, and an inflation cannula outlet;
    the inflation cannula body being laterally connected to the main cannula body;
    the main cannula inlet further comprising a plurality of holes;
    the inflation cannula body further comprising an inflation valve;
    the inflation cannula inlet being positioned adjacent to the main cannula outlet;
    the occluding ballon being positioned about the center along the length of the main cannula body;
    each of the plurality of markings being equally spaced from one another;
    the plurality of holes being radially distributed about the main cannula inlet;
    the plurality of holes being distributed along only the main cannula inlet up until the occluding balloon;
    the inflation cannula outlet hermetically traversing into the occluding balloon;
    the inflation cannula inlet being positioned offset from the main cannula outlet;
    the inflation valve being in fluid communication with the inflation cannula; and
    the inflation valve being positioned adjacent to the inflation cannula inlet.

2. The venous drainage catheter for normothermic regional perfusion as claimed in claim 1 comprising:
    the main cannula body further comprising a plurality of markings; and
    the plurality of markings traversing radially about the main cannula body.

3. The venous drainage catheter for normothermic regional perfusion as claimed in claim 2 comprising:
    the plurality of markings being positioned adjacent to the occluding ballon; and
    the plurality of marking being positioned along the main cannula body in between the main cannula outlet and the occluding balloon.

4. The venous drainage catheter for normothermic regional perfusion as claimed in claim 1 wherein
    the plurality of holes traversing through the main cannula inlet.

5. The venous drainage catheter for normothermic regional perfusion as claimed in claim 1 wherein
    the occluding balloon being laterally connected around the main cannula body.

6

6. The venous drainage catheter for normothermic regional perfusion as claimed in claim 1 comprising:
    a cardiopulmonary circuit; and
    the cardiopulmonary circuit further comprising a reservoir, a membrane oxygenator, a pump, and at least one aortic cross clamp.

7. The venous drainage catheter for normothermic regional perfusion as claimed in claim 6 wherein the main cannula outlet being in fluid communication with the reservoir.

8. A venous drainage catheter for normothermic regional perfusion comprising:
    at least one main cannula;
    an inflation cannula;
    an occluding balloon;
    the at least one main cannula comprising a main cannula body, a main cannula inlet, and a main cannula outlet;
    the inflation cannula comprising an inflation cannula body, an inflation cannula inlet, and an inflation cannula outlet;
    the inflation cannula body being laterally connected to the main cannula body;
    the main cannula inlet further comprising a plurality of holes;
    the inflation cannula body further comprising an inflation valve;
    the inflation cannula inlet being positioned adjacent to the main cannula outlet;
    the occluding ballon being positioned about the center along the length of the main cannula body;
    the main cannula body further comprising a plurality of markings;
    the occluding balloon being laterally connected around the main cannula body;
    each of the plurality of markings being equally spaced from one another;
    the plurality of holes traversing through the main cannula inlet; and
    the plurality of holes being distributed along only the main cannula inlet up until the occluding balloon with none of the plurality of holes being distributed along the main cannula outlet.

9. The venous drainage catheter for normothermic regional perfusion as claimed in claim 8 comprising:
    the plurality of markings traversing radially about the main cannula body;
    the plurality of markings being positioned adjacent to the occluding ballon.

10. The venous drainage catheter for normothermic regional perfusion as claimed in claim 9 wherein the plurality of marking being positioned along the main cannula body in between the main cannula outlet and the occluding balloon.

11. The venous drainage catheter for normothermic regional perfusion as claimed in claim 8 wherein:
    the plurality of holes being radially distributed about the main cannula inlet.

12. The venous drainage catheter for normothermic regional perfusion as claimed in claim 8 comprising:
    the inflation cannula outlet hermetically traversing into the occluding balloon; and
    the inflation cannula inlet being positioned offset from the main cannula outlet.

13. The venous drainage catheter for normothermic regional perfusion as claimed in claim 8 comprising:
    the inflation valve being in fluid communication with the inflation cannula; and the inflation valve being positioned adjacent to the inflation cannula inlet.

14. The venous drainage catheter for normothermic regional perfusion as claimed in claim 8 comprising:
    a cardiopulmonary circuit; and
    the cardiopulmonary circuit further comprising a reservoir, a membrane oxygenator, a pump, and at least one aortic cross clamp.

15. The venous drainage catheter for normothermic regional perfusion as claimed in claim 14 wherein the main cannula outlet being in fluid communication with the reservoir.

16. A venous drainage catheter for normothermic regional perfusion comprising:
    at least one main cannula;
    an inflation cannula;
    an occluding balloon;
    the at least one main cannula comprising a main cannula body, a main cannula inlet, and a main cannula outlet;
    the inflation cannula comprising an inflation cannula body, an inflation cannula inlet, and an inflation cannula outlet;
    the inflation cannula body being laterally connected to the main cannula body;
    the main cannula inlet further comprising a plurality of holes;
    the inflation cannula body further comprising an inflation valve;
    the inflation cannula inlet being positioned adjacent to the main cannula outlet;
    the occluding ballon being positioned about the center along the length of the main cannula body;
    the main cannula body further comprising a plurality of markings;
    the plurality of markings traversing radially about the main cannula body;

the occluding balloon being laterally connected around the main cannula body
    each of the plurality of markings being equally spaced from one another;
    the plurality of markings being positioned adjacent to the occluding ballon;
    the plurality of marking being positioned along the main cannula body in between the main cannula outlet and the occluding balloon;
    the plurality of holes being radially distributed about the main cannula inlet;
    the plurality of holes traversing through the main cannula inlet;
    the plurality of holes being distributed only along the main cannula inlet up until the occluding balloon with none of the plurality of holes being distributed along the main cannula outlet;
    the inflation cannula outlet hermetically traversing into the occluding balloon; and
    the inflation cannula inlet being positioned offset from the main cannula outlet.

17. The venous drainage catheter for normothermic regional perfusion as claimed in claim 16 comprising:
    the inflation valve being in fluid communication with the inflation cannula; and
    the inflation valve being positioned adjacent to the inflation cannula inlet.

18. The venous drainage catheter for normothermic regional perfusion as claimed in claim 16 comprising:
    a cardiopulmonary circuit;
    the cardiopulmonary circuit further comprising a reservoir, a membrane oxygenator, a pump, and at least one aortic cross clamp; and
    the main cannula outlet being in fluid communication with the reservoir.

* * * * *